United States Patent [19]

Urdea et al.

[11] Patent Number: 4,868,105

[45] Date of Patent: Sep. 19, 1989

[54] SOLUTION PHASE NUCLEIC ACID SANDWICH ASSAY

[75] Inventors: Mickey Urdea, Alamo; Brian Warner, Redwood City, both of Calif.

[73] Assignee: Chiron Corporation, Emeryville, Calif.

[21] Appl. No.: 807,624

[22] Filed: Dec. 11, 1985

[51] Int. Cl.[4] ............................................. C12Q 1/68
[52] U.S. Cl. ...................................... 435/6; 435/810; 536/27; 935/77; 935/78
[58] Field of Search ...................... 435/6.810; 536/27; 935/78, 77

[56] References Cited

U.S. PATENT DOCUMENTS

| | | | |
|---|---|---|---|
| 4,563,417 | 1/1986 | Albarella | 935/77 |
| 4,716,106 | 12/1987 | Chiswell | 435/6 |
| 4,731,325 | 3/1988 | Palva et al. | 435/6 |
| 4,751,177 | 6/1988 | Stabinsky | 435/6 |

FOREIGN PATENT DOCUMENTS

| | | | |
|---|---|---|---|
| 123300 | 10/1984 | European Pat. Off. | |
| 0128332 | 12/1984 | European Pat. Off. | 435/6 |
| 0139489 | 5/1985 | European Pat. Off. | 435/6 |
| 0831459 | 4/1983 | PCT Int'l Appl. | |
| 18301459 | 4/1983 | PCT Int'l Appl. | |
| 0843285 | 8/1984 | PCT Int'l Appl. | |
| 8403520 | 9/1984 | PCT Int'l Appl. | |
| 8606412 | 11/1986 | PCT Int'l Appl. | 435/6 |
| 215607 | 10/1985 | United Kingdom | |
| 2169403 | 7/1986 | United Kingdom | 435/6 |

OTHER PUBLICATIONS

Leary et al., *Proc. Natl. Acad. Sci. U.S.A.* 80:4045–4049 (1983).
McBride and Caruthers, *Tet. Lett.* 24(3): 245–248 (1983).
Meinkoth and Wahl, *Anal. Biochem.* 138: 267–284 (1984).
Ranki et al., "Nucleic Acid Sandwich Hybridization in Adenovirus diagnosis" in New Developments in Diagnostic Virology, New York: Springer-Verlag (1983).
Ranki et al., *Gene* 21: 77–85 (1983).
Renz and Kurz, *Nuc. Acids. Res.* 12(8): 3435–3444 (1984).
Richardson and Gumport, *Nuc. Acids. Res.* 11(8): 6167–6184 (1983).
Sanchez-Pescador and Urdea, *DNA* 3(4): 339–343 (1984).
Smith et al., *Nuc. Acids. Res.* 13(7): 2399–2412 (1985).
Syvanen et al., *Nuc. Acids. Res.* 14(12): 5037–5047 (1986).
Valenzuela et al., "The Nucleotide Sequence of the Hepatitis B Viral Genome and the Identification of the Major Viral Genes" in *Animal Virus Genetics*, New York: Academic Press, 1980.
Virtanen et al., The Lancet, pp. 381–383 (Feb. 19, 1983).
Warner et al., *DNA* 3(5): 401–411 (1984).

*Primary Examiner*—Robert J. Warden
*Assistant Examiner*—Robert Benson
*Attorney, Agent, or Firm*—Irell & Manella

[57] ABSTRACT

Methods and compositions are provided for rapid detection of nucleic acid sequences. The method employs two reagent sets. The first set is a labelling set comprising: (1) a first nucleic acid sequence probe having an analyte complementary region and a first recognition sequence region and (2) a labelled sequence complementary to the first recognition sequence region. The second set is a capturing set comprising: (1) a second nucleic acid sequence probe having an analyte complementary region and a second recognition sequence region, (2) a specific binding pair member conjugated to a sequence complementary to the second recognition sequence, and (3) a separating means to which is bound a complementary specific binding pair member. The sample and probes are combined under annealing conditions, followed by addition of the other reagents, separation of the bound label from the supernatant and detection of the label in either phase.

21 Claims, 1 Drawing Sheet

SOLUTION PHASE NUCLEIC ACID SANDWICH ASSAY

BACKGROUND OF THE INVENTION

1. Field of the Invention

The increasing ease of cloning and synthesizing DNA sequences has greatly expanded opportunities for detecting particular nucleic acid sequences of interest. No longer must one rely on the use of immunocomplexes for the detection of pathogens, lesions, antigens, and the like. Rather than detecting particular determinant sites, one can detect DNA sequences or RNA sequences associated with a particular cell. In this manner, diseases can be diagnosed, phenotypes and genotypes can be analyzed, as well as polymorphisms, relationships between cells, and the like.

For the most part, analyses of DNA sequences have involved the binding of a sequence to a solid support and hybridization of a complementary sequence to the bound sequence. The annealing and complexing step usually involves an extended period of time and requires careful washing to minimize non-specific background signals. There is substantial interest in developing new techniques for analyzing nucleic acid sequences, which are more rapid, minimize the number of manipulative steps, and provide for an increased signal to noise ratio.

2. Description of Relevant Literature

Meinkoth and Wahl, *Anal. Biochem.*, (1984) 138:267-284, provide a review article of hybridization techniques. See also Leary et al., *Proc. Natl. Acad. Sci. USA* (1983) 80:4045-4049, for a description of the dot-blot assay. Sandwich hybridization is described by Ranki et al., *Curr. Top. Microbiol. Immunology* (1983) pp. 308ff. See also Ranki et al., *Gene* (1983) 21:77-85, Virtanen et al., *Lancet* (1983) 381-383, and U.S. Pat. No. 4,486,539. EPA 123,300 describes biotin-avidin complexes for use in detecting nucleic acid sequences.

SUMMARY OF THE INVENTION

Methods and compositions are provided for detecting particular nucleic acid sequences. Two sets of reagents are employed, which are referred to as the capturing set and the labelling set. Each set has at least two members. The labelling set has (1) a first probe set, which comprises one or a group of first analyte complementary sequence-first label reagent recognition sequence conjugate(s); and (2) one or a group of sequences complementary to said first recognition sequence-label conjugate(s). The capturing set has (1) a second probe set, which comprises one or a group of second analyte complementary sequence(s) joined to second capturing reagent polynucleotide recognition sequence(s); (2) one or a group of sequences complementary to said second capturing recognition sequence(s) bound to a separation member or preferably a first specific binding pair member to define the capturing conjugate; and (3) a separation member joined to a first complementary specific binding pair member when (2) does not have the separation member.

The single stranded nucleic acid sample may be joined with the probes containing the complementary sequences of the two sets under annealing conditions, followed by the addition of the capturing and optionally the labelling conjugates to provide for the analyte complex with the specific binding pair member and optionally the label. The probe hybridized analyte sequence is separated by combining the complex with the separating means and separating probe bound analyte from unbound analyte. Where the label has not been previously added, the first recognition sequence-label conjugate is added to the phase containing the separation member under hybridizing conditions. The label may then be detected in either phase.

DESCRIPTION OF THE SPECIFIC EMBODIMENTS

Methods and compositions are provided for detecting a nucleic acid sequence by employing two sets of reagents. By using combinations of nucleic acid sequences complementary to a nucleic acid analyte and to arbitrary sequences and specific binding pair members, a detectable label may be separated into two phases in proportion to the amount of analyte present in a sample. By providing for annealing of nucleic acid sequences in solution, the time for performing the assay can be substantially diminished as compared to annealing on a solid surface and the number of separations and washing steps required can be limited and be less critical, so as to reduce technician error. Reagents containing complementary sequences can be added in excess during or at the end of the denaturation to inhibit renaturation of double stranded DNA and to react rapidly with the analyte strand by diffusion in solution. The rate of binding to the solid support can also be accelerated by the presence of a large amount of the binding pair member bound to the support. In addition, by adding the label conjugate as the last reagent, the analyte will be present in a highly concentrated form.

As indicated above, the method involves two sets of reagents. The first set results in labelling the analyte sequence. The second set provides the means for separating label bound to analyte from unbound label in the assay medium.

The first set, the labelling set, will involve at least two reagents and may involve 10 to 30 reagents or more. The first reagent will be a subset of nucleic acid reagents and each member of the subset will have two nucleic acid regions. The first nucleic acid region of each member of the subset will be a region complementary to a sequence of the analyte. The second nucleotide sequence will be a recognition site for the labelling reagent. This second sequence will be selected, so as not to be encountered by endogenous sequences in the sample.

The subsets will have regions complementary to the analyte sequence of at least 15 nucleotides (nt), usually at least 25 nt, more usually at least 50 nt, and not more than about 5 kb, usually not more than about 1 kb, preferably not more than about 100 nt. The sequence complementary to the analyte may be joined to a non-specific sequence at either or both the 5'-and 3'-termini. The non-complementary sequence, if judiciously selected so as not to bind to sequences in the assay which could result in false positives, can be of any length, usually fewer than 10 kb, more usually fewer than 5 kb.

The complementary sequences will be chosen so as to leave areas for binding of the other reagents to the analyte. Usually, areas of at least 25 nt will be available, where the analyte sequences complementary to the sequences of the individual members of the reagent subset may be substantially contiguous or separated and members of one subset may alternate with members of the other subset. The particular pattern of binding between the two subsets may vary widely depending on the sequences of the analyte.

The reagent sequences may be prepared by synthesis in accordance with conventional procedures or by cloning and may be modified as appropriate for labelling.

The set of sequences which are complementary to the analyte may be selected based on a variety of considerations. Depending upon the nature of the analyte, one may be interested in a consensus sequence, a sequence associated with polymorphisms, a particular phenotype or genotype, a particular strain, or the like. Thus, the labelling complementary sequences will be chosen in conjunction with the other complementary sequences of the capturing set to provide information concerning the analyte.

The labelled sequence will include a sequence complementary to the first recognition sequence of the labelling probe(s). The labelling sequence will include one or more molecules, which directly or indirectly provide for a detectable signal. The labels may be bound to individual members of the complementary sequence or may be present as a terminal member or terminal tail having a plurality of labels. Various means for providing labels bound to the sequence have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids Res.* (1985) 13:2399; Meinkoth and Wahl, *Anal. Biochem.* (1984) 138:267. The labels may be bound either covalently or non-covalently to the complementary sequence.

Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$-galactosidase, horseradish peroxidase, etc.

The labelled sequence can be conveniently prepared by synthesis. By providing for a terminal group which has a convenient functionality, various labels may be joined through the functionality. Thus, one can provide for a carboxy, thiol, amine, hydrazine or other functionality to which the various labels may be joined without detrimentally affecting duplex formation with the sequence. As already indicated, one can have a molecule with a plurality of labels joined to the sequence complementary to the labelling sequence. Alternatively, one may have a ligand bound to the labelling sequence and use a labelled receptor for binding to the ligand to provide the labelled analyte complex.

The second set of reagents provides the means for separation of label bound to analyte from unbound label. The means for the separation or capturing means involves at least one capturing probe, usually a plurality of probes defining a subset, which includes two polynucleotide sequence regions that include a second subset of sequences complementary to the analyte, differing from the first subset of complementary sequences of the labelling probe and a recognition sequence, different from the first subset recognition sequence of the labelling probe. The second set of recognition sites for the capture probes may lie between the first set of recognition sites for the labelling probes as described above. The capturing sequences will be selected and synthesized in the same manner as described above using the considerations directing the selection for the labelling probes. Thus, the same constraints will be involved in preparing the capturing probes.

While the separating means may be directly bound to a sequence complementary to the capturing recognition sequence, preferably a specific binding pair member will be bound to the complementary sequence. The specific binding pair member will be a ligand or receptor, preferably a ligand. Ligands may be any molecules for which a naturally-occuring receptor exists or can be prepared. Thus, naturally-occurring ligands may be exemplified by biotin, thyroxine, enzyme substrates, steroids, and the like. Instead of naturally-occurring ligands, any hapten may be employed for the production of antibodies. Ligands will generally be at least about 125 molecular weight and usually less than about 5,000 molecular weight, more usually less than about 2,000 molecular weight, and preferably less than about 1,000 molecular weight.

The receptors will generally be protein molecules and may include antibodies, naturally-occurring proteins, such as avidin, thyroxine binding globulin, etc., lectins, enzymes, and the like. The receptors will generally be at least about 10,000 molecular weight, more usually 12,000 or more molecular weight, usually less than about one million molecular weight.

The specific binding pair member may be joined to the second recognition sequence by any convenient means. As already indicated, the sequence may be synthesized, providing for a convenient functionality at the terminal base, which may then be used as the linkage site. One or a plurality of specific binding pair members may be joined to the complementary sequence, depending upon the particular choice of the specific binding pair member, its size, and the nature of the functionalities. Alternatively, for a large specific binding pair member, a plurality of sequences may be joined to the binding pair member. The capturing conjugate will be prepared, so that there will be little interference, if any, from the specific binding pair member with the annealing of the complementary recognition sequences and from duplex formation with the ligand-receptor binding.

Alternatively, the receptor may be an additional nucleotide sequence that specifically recognizes the recognition sequence of the capture probe.

The separation means can be any support which allows for a rapid and clean separation of label bound to analyte from unbound label. Thus, the separation means may be particles, a solid wall surface of any of a variety of containers, e.g., centrifugal tubes, columns, microtiter plate wells, filters, tubing, etc. Preferably, particles will be employed of a size in the range of about 0.4 to 200$\mu$, more usually from about 0.8 to 4.0$\mu$. The particles may be any convenient material, such as latex, glass, etc.

The homologous nucleic acid sequences need not have perfect complementarity to provide homoduplexes. In many situations, heteroduplexes will suffice where fewer than 15%, usually fewer than 10% of the bases are mismatches, ignoring loops of five or more members.

Samples of analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher.

In carrying out the method, the analyte sequence will be provided in single stranded form. Where the sequence is naturally present in single stranded form, denaturation will not be required. However, where the sequence is present in double stranded form, the sequence will be denatured. Denaturation can be carried out by various techniques, such as alkali, generally from about 0.05 to 0.2M hydroxide, formamide, detergents, heat, or combinations thereof. Denaturation can be carried out in the presence of the labelling probe and/or the capturing probe, so that upon change of conditions to annealing conditions, the probes will bind to any complementary sequences which are present. For example, where heat and alkali are employed, by neutralization and cooling, annealing will occur.

In many situations, it will be preferable to avoid having either the label or the separation means present during denaturation. The elevated temperatures, the non-aqueous solvents, the salts, or other materials present during denaturation may result in degradation, or undesirable modification of the label and/or separation means. Therefore, in many situations, denaturation may occur in the presence of the probes, whereupon cooling rapid annealing of the probes to the single-stranded DNA may occur, followed by the addition of the other reagents at lower temperatures and, as appropriate, under milder conditions, such as neutral pH, reduced ionic strength, or the like.

Normally, the ratio of probe to anticipated moles of analyte will be at least 1:1, preferably at least about 1.5:1, and more preferably 2:1 and may be as high as 100:1 or higher. Concentrations of each of the probes will generally range from about $10^{-9}$ to $10^{-6}$M, with sample nucleic acid concentrations varying from $10^{-21}$ to $10^{-12}$M.

After annealing conditions have been achieved, or even prior to such time, the labelled first recognition sequence and the capturing second recognition sequence are added and allowed to hybridize. Alternatively, the labelled first recognition sequence can be added after capture and separation.

A preferred embodiment which greatly reduces background and provides for extraordinarily high sensitivity will employ the following sequence. With double-stranded analyte, the analyte will be denatured in the presence of the probe or complementary sequences, or the probes may be added shortly after denaturation, and under annealing conditions. After sufficient time for annealing, the complexes may then be combined with the separation means, whereby the complexes will be bound to the support. Any background DNA or non-specifically bound DNA may be washed away so as to avoid non-specific binding of label in the next step. The solid support may then be washed to remove any non-specifically bound label to provide for a substantially reduced background of non-specifically bound label.

Figure 1A:
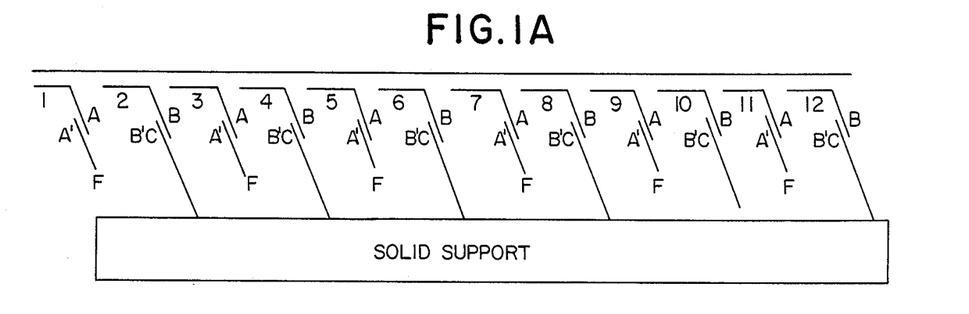
FIGS. 1a and 1b are illustrative depictions of a complex from the various components bound to a solid support (1a) using DNA bridges for non-covalent binding or (1b) using biotin-avidin bridges for non-covalent binding.
Figure 1B:
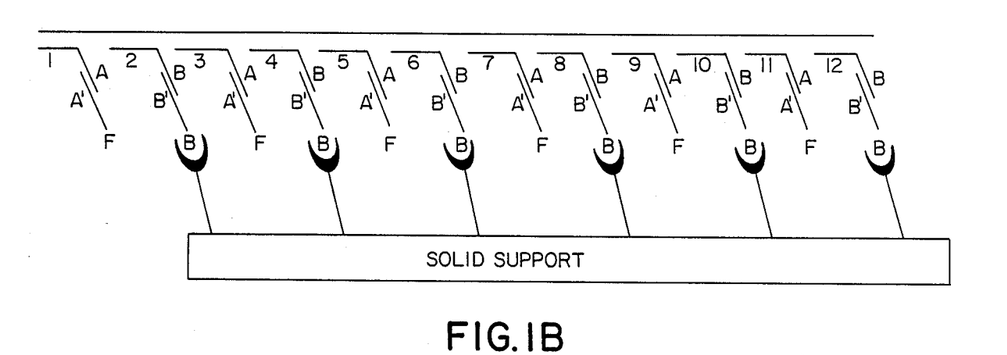

Consider FIG. 1, part 2. In effect, the analyte which is the long bar at the top is combined with the A and B probes, where A provides the complementary sequence for the label conjugate and B provides the complementary sequence for the specific binding pair member, in this case, biotin. Thus, the A and B probes and the analyte would be joined together under annealing conditions, whereby complex formation would occur between the probes and the analyte. The biotin conjugate, B' could be included with the probes or be added in a separate step to the solution containing the analyte complexes. After sufficient time for B' to anneal to B, the resulting biotinylated analyte complex would then be added to the solid support to which avidin is bound. After sufficient time for the specific binding pair members to form complexes, the solid support could be washed free of any non-specific DNA, followed by the addition of the labeled sequence, which in this case is indicated as being fluorescein bound to A'. The labeled sequence would be added under annealing conditions and after sufficient time for duplex formation, non-specifically bound and excess labeled conjugate would be washed away and the fluorescence of the surface determined.

A somewhat shorter protocol is provided by the configuration depicted in part 1 of FIG. 1. In this situation, the probes A and B would be added to the analyte under annealing conditions, whereby analyte complexes would form. After sufficient time for analyte complexes to form, the analyte complex solution would then be added to the solid support for sufficient time for the capturing probes to bind to the solid support by complex formation with the sequence indicated as B'C. Excess DNA could be washed away, followed by the addition of the fluorescein labeled sequence A', and the mixture allowed to anneal for sufficient time for complex formation to occur between the label and the probes. Excess in non-specifically bound label could then be washed away to provide the configuration depicted in FIG. 1, part 1.

Usually, the denaturing step will take from about 5 to 25 minutes, usually from about 5 to 15 minutes, while the annealing step will generally take from about 30 minutes to 2 hours, frequently being completed in about 1 hour. Annealing can be carried out at a mildly elevated temperature, generally in the range from about 20° C. to 50° C., more usually from about 25° C. to 40° C., particularly 37° C.

Usually, an aqueous medium is employed, particularly a buffered aqueous medium, which may include various additives. Additives which may be employed include low concentrations of detergent (0.1 to 1%), salts, e.g., sodium citrate (0.017 to 0.17M), Ficoll, polyvinylpyrrolidine, carrier nucleic acids, carrier proteins, etc. Depending upon the nature of the specific binding pair members, various solvents may be added to the aqueous medium, such as dimethylformamide, dimethylsulfoxide, and formamide. These other solvents will be present in amounts ranging from 2 to 50%.

The stringency of the annealing medium may be controlled by temperature, salt concentration, solvent system, and the like. Thus, depending upon the length and nature of the sequence of interest, the stringency will be varied.

For the separation step, for example, using a ligand-receptor pair, the medium may be changed to optimize or approximately optimize the conditions for specific binding pair complex formation. Thus, the pH will usually be modified to be in the range of about 6 to 9, preferably about 7. This can be readily achieved, by adding from about 0.5 to 2, usually about 1 volume of about a 0.1 to 0.5M buffered medium, e.g., phosphate buffered saline, to the annealing medium. This medium may be added in conjunction with the separation means and the mixture allowed to incubate for at least 5 min., usually about 10 min., and less than about 60 min., usually about 15 to 45 min., more usually about 30 min. being satisfactory.

The phases may then be separated in accordance with the nature of the separation means. For particles, centrifugation or filtration will provide for separation of the particles, discarding the supernatant or isolating the supernatant. Where the particles are assayed, the particles will be washed thoroughly, usually from one to five times, with an appropriate buffered medium, e.g., PBS. When the separation means is a wall or support, the supernatant may be isolated or discarded and the wall washed in the same manner as indicated for the particles.

Depending upon the nature of the label, various techniques can be employed for detecting the presence of the label. For fluorescers, a large number of different fluorometers are available. With enzymes, either a fluorescent or a colored product can be provided and determined fluorometrically, spectrophotometrically or visually. The various labels which have been employed in immunoassays and the techniques applicable to immunoassays can be employed with the subject assays.

The following examples are offered by way of illustration and not by way of limitation.

Analyte BglII HBV Fragment

```
GATCTCC |TAGACACCGCCTCAGCTCTGTATCGAGAAG |CCT |TAGAGTCTCCTGAG
    AGG |ATCTGTGGCGGGAGTCGAGACATAGCTCTTC |GGA |ATCTCAGAGGACTC
        →            1                    ← →           2

CATTGCTCACCTCACC |ATA |CTGCACTCAGGCAAGCCATTCTCTGCTGGG |GGG |AATTGATG
GTAACGAGTGGAGTGG |TAT |GACGTGAGTCCGTTCGGTAAGAGACGACCC |CCC |TTAACTAC
      ← →              3                               ← →

ACTCTAGCTACCTGGGTGGGTA |ATA |ATTTGGAAGATCCAGCATCTAGGGATCTTG |TAG |TA
TGAGATCGATGGACCCCACCCAT |TAT |TAAACCTTCTAGGTCGTAGATCCCTAGAAC |ATC |AT
         4              ← →              5                   ← →

ACTCTAGCTACCTGGGGGGTA |ATA |ATTTGGAAGATCCAGCATCTAGGGATCTTG |TAG |TA
TGAGATCGATGGACCCCACCCAT |TAT |TAAACCTTCTAGGTCGTAGATCCCTAGAAC |ATC |AT
         4              ← →              5                   ← →

AATTATGTTAATACTAACGTGGGTTTAA |AGA |TCAGGCAACTATTGTGGTTTCATATATCT
TTAATACAATTATGATTGCACCCAAATT |TCT |AGTCCGTTGATAACACCAAAGTATATAGA
              6               ← →                  7

T |GCC |TTACTTTTGGAAGAGAGACTGTACTTGAAT |ATT |TGGTCTCTTTCGGAGTGTGGATT
A |CGG |AATGAAAACCTTCTCTCTGACATGAACTTA |TAA |ACCAGAGAAAGCCTCACACCTAA
 ← →              8                      ← →             9

CGCACTC |CTC |CAGCCTATAGACCACCAAATGCCCCTATCT |TAT |CAACACTTCCGGAAACT
GCGTGAG |GAG |GTCGGATATCTGGTGGTTTACGGGGATAGA |ATA |GTTGTGAAGGCCTTTGA
 ← →              10                          ← →             11

ACTGTTGTTAGAC |GAC |GGGACCGAGGCAGGTCCCCTAGAAGAAGAA |CTCCCTCGCCTCGC
TGACAACAATCTG |CTG |CCCTGGCTCCGTCCAGGGGATCTTCTTCTT |GAGGGAGCGGAGCG
     ← →              12                            ←

AGACGCA
TCTGCGTGTAG

→ ← — indicates probed segments
```

Labelling and Capturing Probe Sets (Refer to FIG. 1)

```
3'  GACTTGCAAGTTGGTCAAGT |ATCTGTGGCGGAGTCGAGACATAGCTCTTC |  5'
            A                           1
            →                           ←

GTGGTGAAAGAGGTTTCTTC |ATCTCAGAGGACTCGTAACGAGTGGAGTGG |
            B                           2
            →                           ←
```

| —> Labeled Probe <— | —> Probe segments to HBV <— | recognition sequences

A - Fluorescein label conjugate binding site
B - Biotin or DNA conjugate binding site Label conjugate (A') for DNA or avidin support:
    Fluorescein - 5' CTGAACGTTCAACCAGTTCA 3'

DNA sequence (B'C) bound to solid support:
3' GAAGAAACCTCTTTCACCACTGTCATCAAAAGGTTAACCATGTTTCTTGT 5'

Biotin conjugate (B') for avidin support:
    Biotin - 5' CACCACTTTCTCCAAAGAAG 3'

Preparation of biotin or fluoroscein labeled DNA (A' or B'):

$N^4$—(2′-aminoethyl-deoxycytosine-DNA)

The analyte is an HBV BglII fragment as indicated above. (Valenzuela et al. (1981) in Animal Virus Genetics, eds. Fields, B., Jaenisch, R., Fox, C.F., Academic Press, Inc., N.Y., pp 57–70.) A subset of labelling and capturing probes are indicated, where 12 different sequences complementary to different sequences present in HBV are provided. Six of the HBV complementary sequences are joined to a common sequence (A) for complexing with the label conjugate (A′). The other six HBV complementary sequences are joined to a common sequence (B) for complexing with a biotinylated sequence (B′) or a third DNA sequence (B′C) for binding to a support. In FIG. 1 is shown an illustration of the final complex involving the HBV strand and the various reagents.

Preparation of Succinimidyl N-6(N-5 Thioureidyl Fluorescein) Caproate (I)

To 1 mmole of fluorescein isothiocyanate in 5 ml of DMF was added 2 mmole of 6-aminocaproic acid and 540μl of triethylamine. After 24 h at room temperature, the product was isolated by preparative thin layer chromatography (Warner and Legg, Inorg. Chem. (1979) 18:1839). The dried product was suspended in 10 ml of DMF/THF 1:1 (v/v) to which 1.5 mmole of N-hydroxy succinimide and 1 mmole of dicyclohexycarbodiimide were added. After 18 h at room temperature the solution was filtered through glass wool and diluted to a 0.2M final concentration with DMF (assuming a 100% yield from step 1).

Preparation of $N^4$-(2′-aminoethyl) Deoxycytidine.

An alkylated derivative of deoxycytosine, $N^4$-(2′-aminoethyl) deoxycytosine (II), was prepared from properly protected deoxyuridine via the 4-tetrazoyl derivative as described by Reese and Ubasawa, Tet. Lett. (1984) 21:2265. This latter derivative was converted to (II) by displacement of the tetrazoyl moiety with ethylene diamine essentially as described by Sung, J. Org. Chem. (1982) 47:3623 and Maggio et al., Tet. Lett. (1984) 25:3195. The corresponding 5′-DMT 3′-phosphoramidite $N^4$-(2-N-trifluoroacetylaminoethyl) deoxycytosine was prepared by blocking the alkylamine with trifluoroacetic anhydride and then preparation of the corresponding N,N-diisopropyl phosphoramidite as described (Beaucage and Caruthers, Tet. Lett. (1982) 22:1859; McBride and Caruthers, Tet. Lett. (1983) 24:245).

Preparation of Fluorescein Labelled Probes.

Synthetic oligonucleotides were prepared by an automated phosphoramidite method as described in Warner et al., DNA (1984) 3:401. Purification was carried out according to Sanchez-Pescador and Urdea, DNA (1984) 3:339.

The aminoethyl derivative of deoxycytidine was incorporated by standard coupling procedures during the oligonucleotide synthesis and the purified modified oligonucleotides were used for incorporation of a fluorescein label as follows. To a dried sample (3–5 OD 260 units) of the aminoethyl deoxycytidine containing oligomer were added 50μl of 0.1M sodium phosphate pH 7.0, 50μl of DMF and 25μl of the 0.2M stock solution of I described above. After 18 h at room temperature, the solution was partially purified by Sephadex G-10 chromatography in water, dried and further purified by polyacrylamide gel, as above.

Preparation of Biotin Labelled Probes.

Using $N^4$-(aminoethyl) deoxycytidine containing probes prepared as described above, biotin labeling was achieved as follows. The oligonucleotide (3–5 OD 260 units) was taken up in 50μl 0.1M sodium phosphate, pH 7.0 and 50μl DMF to which 100μl of a DMF solution containing 1 mg of "long chain" succinimidyl biotin (Pierce Chemical) was added. After 18 h at room temperature, the biotinylated probe was purified as described for the fluorescein labeled probe.

Preparation of Solid-Supported DNA Probe.

Fragment B′C (a synthetic 50 mer) was 5′-phosphorylated with T4-polynucleotide kinase and ATP using standard conditions. After gel purification as described above, the oligonucleotide was dried by evacuation.

Hydroxylated latex (10 mg; 0.8μ; Pandex Laboratories) was washed with DMSO, then three portions of 40 mM MES (morpholinoethanesulfonic acid), pH 6.0 by centrifugation. 1500 pmoles of 5′-phosphorylated fragment B′C was taken up in 90μl of 40 mM MES and added to the washed support. A solution was prepared to contain 100 mg of EDAC in 100μl of MES. After adding 5μl of the EDAC solution and mixing, the reaction mixture was evaporated until 30μl total remained. The mixture was left at 37° C. for 18 h, then centrifuged for 2 min at 12,000 rpm. The supernatant was discarded. The latex was suspended in 30μl of DMSO, vortexed, 100μl of water was added, the mixture vortexed for 2 min and the supernatant was discarded after centrifugation. This washing process was repeated twice. The support was then washed three times with 100μl portions of 4×SSC, H₂O, then H₂O at 37° C. for 15 min (yield 20 picomoles fragment B'C per mg of latex).

Assay for HBV DNA Using DNA Solid Support.

A pBR322 clone containing the entire HBV genome (Valenzuela et al., *Animal Virus Genetics*, R. Jaenisch, B. Fields and C.F. Fox, Eds. (Academic Press: New York) pp. 57–70 (1980)) was cut with BglII and used as the analyte nucleic acid. Analyte in 10μl of formamide containing 6 picomoles of the labelling and capturing probe sets was heated to 95° C. for 10 min and cooled to room temperature. To this mixture, 60μl of water, 20μl of 20×SSC, 10μl of 1% NP40 and 2μl (10μg) of polyA are added, vortexed and incubated at 37° C. for 1 h.

The solid supported DNA probes (8 picomoles 400μg) is added and incubated for an additional 1.5 h. The mixture is centrifuged at 12,000 rpm for 2 min and the supernatant discarded. The support is washed once by vortexing the pellet into solution with 100μl of 4×SSC, followed by centrifugation. To the washed beads are added a mixture of 4μl of 20×SSC, 2μl of 1% NP40, 1μl (5μg) polyA, 13μl of water and 6 picomoles of fluorescein labeled probe. After incubation at 37° C. for 30 min, the beads are transfered to a Pandex filter plate, washed four times with 100μl of 4×SSC by vacuum filtration on the 0.2μ cellulose acetate membrane of the plate. The sample is vacuumed to dryness and read on the fluorescein channel A ($\lambda_{excitation}$—485; $\lambda_{emission}$—525) of the Pandex screen machine.

TABLE 1

| Condition | Fluorescence Counts (Average of 4) |
|---|---|
| 0.5 pmole HBV | 5062 ± 345 |
| 0.25 pmole HBV | 4117 ± 262 |
| No Analyte | 3197 ± 520 |
| No Biotinylated Probe | 3856 ± 642 |

ASSAY FOR HBV DNA USING AVIDIN SUPPORT

Experiment 1

Analyte was mixed and incubated with the labelling and capturing probes as above. Biotin labeled probe (12 picomoles) in 5μl H₂O was then added, vortexed and incubated at 37° C. for 30 min. To the mixture, 20μl of a 0.25% (w/v) 0.8μ avidin latex (Pandex Laboratories) in 1×PBS is added and incubated at 37° C. for 1 h. The mixture is washed, incubated with fluorescein probe, washed and read on the Pandex screen machine as described above.

TABLE 2

| Condition | Fluorescence Counts (Average of 4) |
|---|---|
| 0.5 picomole HBV | 4052 ± 462 |
| 0.25 picomole HBV | 2644 ± 397 |
| 0.10 picomole HBV | 1956 ± 173 |
| No Analyte | 1641 ± 370 |
| No Biotinylated Probe | 1631 ± 474 |

Experiment 2

The HBV plasmid was sonicated to an average size of 500 bp. The denaturation and hybridization were carried out as above except that 30 picomoles of labelling and capturing probes were used and a 5 h annealing was employed. After incubation with 30 picomoles of biotinylated probe (2 h), 50μl of 0.25% avidin beads were added and incubated (1.5 h). A fluorescein probe was added and incubation was carried out for 1 h followed by washing and reading on the Screen Machine as described above.

TABLE 3

| Condition | Fluorescence Counts (Average of 4) |
|---|---|
| 0.5 picomole HBV | 5748 ± 244 |
| 0.4 picomole HBV | 5352 ± 331 |
| 0.3 picomole HBV | 4716 ± 243 |
| 0.2 picomole HBV | 4071 ± 243 |
| 0.1 picomole HBV | 3320 ± 271 |
| No Analyte | 1679 ± 167 |
| No Biotinylated Probe | 1716 ± 177 |

It is evident from the above results that a highly specific sensitive assay for specific nucleic acid sequences is provided. Reagents can be readily prepared to the sequence of interest and with a few simple manipulative steps, the presence or absence of a sequence in a sample determined. The method is versatile in permitting a wide variety of labels which can be readily determined by conventional equipment. Probes can be synthesized to the desired length and easily linked to the label or a support. Universal sequences can be prepared for the label and binding to the support. Various protocols may be employed where more or less rigorous removal of background interference is achieved depending upon the requirements of the assay.

Although the foregoing invention has been described in some detail by way of illustration and example for purposes of clarity of understanding, it will be obvious that certain changes and modifications may be practiced within the scope of the appended claims.

What is claimed is:

1. An assay method for detecting a nucleic acid analyte in a sample, employing two sets of reagents, a labelling set and a capturing set, said method comprising:

(1) providing members of said labelling set of reagents, comprising:

(a) a plurality of labelling nucleic acid probes comprising single-stranded polynucleotide chains each having two nucleic acid regions, the first region having a nucleic acid sequence L-1 about 15 to about 100 nucleotides in length which is complementary to a sequence of said analyte, and the second, noncomplementary region at most about 5 kb in length and including a labelling reagent recognition sequence L-2, wherein each of said sequences L-1 is complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) providing members of said capturing set of reagents, comprising:

(c) a plurality of capturing nucleic acid probes comprising single-stranded polynucleotide chains each having two polynucleotide sequence regions, the first region having a nucleic acid sequence C-1 about 15 to about 100 nucleotides in length and which is complementary to a sequence of said analyte, and the second, noncomplementary region at most about 5 kb in length and including a capturing reagent recognition sequence C-2, wherein said sequences L-1 and C-1 are nonidentical, noncomplementary sequences that are each complementary to physically distinct sequences of said analyte, and wherein each of said sequences C-1 is complementary to physically distinct, nonoverlapping sequences of said analyte; and (d) a capturing reagent having a nucleic acid sequence complementary to said capturing reagent recognition sequence C-2 and containing one member of a specific binding receptor-ligand pair, the other, complementary member of said specific binding pair being covalently bound to a solid support;

(3) combining in a liquid medium under binding conditions for complementary pairs, said sample containing analyte in single-stranded form, with said labelling and capturing probes, to provide probe-analyte complexes;

(4) combining said probe-analyte complexes with said capturing reagent to give support-bound probe-analyte complexes;

(5) washing said support to provide said support-bound probe-analyte complexes substantially free of unbound probe and unbound analyte;

(6) contacting said support with said labelling reagent to label said support-bound probe-analyte complexes;

(7) separating said label into a bound phase and an unbound phase by means of said solid support; and (8) detecting the amount of bound or unbound label as determinative of the presence of said analyte.

2. The method of claim 1, wherein said solid support comprises a plurality of particles.

3. The method of claim 1, wherein said label is a fluorescer or an enzyme.

4. The method of claim 1, wherein said receptor is biotin and said ligand is avidin.

5. An assay method for detecting a nucleic acid analyte in a sample, employing two sets of reagents, a labelling set and a capturing set, said method comprising:

(1) providing members of said labelling set of reagents, comprising:

(a) a plurality of labelling nucleic acid probes comprising single-stranded polynucleotide chains each having two nucleic acid regions, the first region having a nucleic acid sequence L-1 about 15 to about 100 nucleotides in length which is complementary to a sequence of said analyte, and the second, noncomplementary region at most about 5 kb in length and including a labelling reagent recognition sequence L-2, wherein each of said sequences L-1 is complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) providing members of said capturing set of reagents, comprising:

(c) a plurality of capturing nucleic acid probes comprising single-stranded polynucleotide chains each having two polynucleotide sequence regions, the first region having a nucleic acid sequence C-1 about 15 to about 100 nucleotides in length which is complementary to a sequence of said analyte, and the second, noncomplementary region at most about 5 kb in length and including a capturing reagent recognition sequence C-2, wherein said sequences L-1 and C-1 are nonidentical, noncomplementary sequences that are each complementary to physically distinct sequences of said analyte, and wherein each of said sequences C-1 is complementary to physically distinct, nonoverlapping sequences of said analyte; and (d) a capturing reagent having a nucleic acid sequence complementary to said capturing reagent recognition sequence C-2 covalently bound to a solid support;

(3) combining in a liquid medium under binding conditions for complementary pairs, said sample containing analyte in single-stranded form, with said labelling and capturing probes, to provide probe-analyte complexes;

(4) combining said probe-analyte complexes with said capturing reagent to give support-bound probe-analyte complexes;

(5) washing said support to provide said support-bound probe-analyte complexes substantially free of unbound probe and unbound analyte;

(6) contacting said support with said labelling reagent to label said support-bound probe-analyte complexes;

(7) separating said label into a bound phase and an unbound phase by means of said solid support; and (8) detecting the amount of bound or unbound label as determinative of the presence of said analyte.

6. The method of claim 5, wherein said analyte is initially provided in double-stranded form and, prior to said combining, is denatured in the presence of base at elevated temperature.

7. The method of claim 5, wherein said solid support comprises a plurality of particles.

8. The method of claim 5, wherein said label is a fluorescer or an enzyme.

9. An assay method for detecting a nucleic acid analyte in a sample, employing two sets of reagents, a labelling set and a capturing set, said method comprising:

(1) providing members of said labelling set of reagents, comprising:

(a) a plurality of labelling nucleic acid probes comprising single-stranded polynucleotide chains each having two nucleic acid regions, the first region having a nucleic acid sequence L-1 about 15 to about 100 nucleotides in length which is complementary to a sequence of said analyte, and the second, noncomplementary region at most about 5 kb in length and including a labelling reagent recognition sequence L-2, wherein each of said sequences L-1 is complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) providing members of said capturing set of reagents, comprising:

(c) a plurality of capturing nucleic acid probes comprising single-stranded polynucleotide chains each having two polynucleotide sequence regions, the first region having a nucleic acid sequence C-1 about 15 to about 100 nucleotides in length which is complementary to a sequence of said analyte, and the second, noncomplementary region at most about 5 kb in length and including a capturing reagent recognition sequence C-2, wherein said sequences L-1 and C-1 are nonidentical, noncomplementary sequences that are each complementary to physically distinct sequences of said analyte, and wherein each of said sequences C-1 is complementary to physically distinct, nonoverlapping sequences of said analyte; and (d) a capturing reagent having a nucleic acid sequence complementary to said capturing reagent recognition sequence C-2 and containing one member of a specific binding hapten-antibody pair, the other, complementary member of said specific binding pair being covalently bound to a solid support;

(3) combining in a liquid medium under binding conditions for complementary pairs, said sample containing analyte in single-stranded form, with said labelling and capturing probes, to provide probe-analyte complexes;

(4) combining said probe-analyte complexes with said capturing reagent to give support-bound probe-analyte complexes;

(5) washing said support to provide said support-bound probe-analyte complexes substantially free of unbound probe and unbound analyte;

(6) contacting said support with said labelling reagent to label said support-bound probe-analyte complexes;

(7) separating said label into a bound phase and an unbound phase by means of said solid support; and (8) detecting the amount of bound or unbound label as determinative of the presence of said analyte.

10. The method of claim 9, wherein said solid support comprises a plurality of particles.

11. The method of claim 9, wherein said label is a fluorescer or an enzyme.

12. The method of claim 9, wherein said binding of said capturing reagent to said solid support is effected at a pH in the range of about 6 to 9.

13. A kit for detecting a nucleic acid analyte in single-stranded form, comprising:

(1) members of a labelling set of reagents comprising:

(a) a plurality of labelling nucleic acid probes comprising single-stranded polynucleotide chains each having two nucleic acid regions, the first region having a nucleic acid sequence L-1 about 15 to about 100 nucleotides in length and selected so as to be complementary to a sequence of said analyte, and the second, noncomplementary region at most about 5 kb in length and including a labelling reagent recognition sequence L-2, wherein each of said sequences L-1 is selected so as to be complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) members of a capturing set of reagents comprising:

(a) a plurality of capturing nucleic acid probes comprising single-stranded polynucleotide chains each having two polynucleotide sequence regions, the first region having a nucleic acid sequence C-1 about 15 to about 100 nucleotides in length and which is selected so as to be complementary to a sequence of said analyte, and the second, noncomplementary region at most about 5 kb in length and including a capturing reagent recognition sequence C-2, wherein said sequences L-1 and C-1 are nonidentical, noncomplementary sequences that are each complementary to physically distinct sequences of said analyte;

(b) a capturing reagent having a nucleic acid sequence complementary to said capturing reagent recognition sequence C-2 and containing a first member of a specific binding receptor-ligand pair; and (c) a solid support, to which is bound a second member of said specific binding pair, complementary to said first member, enabling separation and detection of said analyte.

14. The kit of claim 13, wherein said receptor is biotin and said ligand is avidin.

15. The kit of claim 13, wherein said solid support comprises a plurality of particles.

16. The kit of claim 13, wherein said label is a fluorescer or an enzyme.

17. A kit for detecting a nucleic acid analyte in single-stranded form, comprising:

(1) members of a labelling set of reagents comprising:

(a) a plurality of labelling nucleic acid probes comprising single-stranded polynucleotide chains each having two nucleic acid regions, the first region having a nucleic acid sequence L-1 about 15 to about 100 nucleotides in length and selected so as to be complementary to a sequence of said analyte, and the second, noncomplementary region at most about 5 kb in length and including a labelling reagent recognition sequence L-2, wherein each of said sequences L-1 is selected so as to be complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) members of a capturing set of reagents comprising:

(a) a plurality of capturing nucleic acid probes comprising single-stranded polynucleotide chains each having two polynucleotide sequence regions, the first region having a nucleic acid sequence C-1 about 15 to about 100 nucleotides in length and which is selected so as to be complementary to a sequence of said analyte, and the second, noncomplementary, region at most about 5 kb in length and including a capturing reagent recognition sequence C-2, wherein said sequences L-1 and C-1 are nonidentical, noncomplementary sequences that are each complementary to physically distinct sequences of said analyte;

(b) a capturing reagent having a nucleic acid sequence complementary to said capturing reagent recognition sequence C-2; and (c) a solid support enabling separation and detection of said analyte, wherein said capturing reagent is covalently bound to said solid support.

18. The kit of claim 17, wherein said solid support comprises a plurality of particles.

19. A kit for detecting a nucleic acid analyte in single-stranded form, comprising:

(1) members of a labelling set of reagents comprising:

(a) a plurality of labelling nucleic acid probes comprising single-stranded polynucleotide chains each having two nucleic acid regions, the first region having a nucleic acid sequence L-1 about 15 to about 100 nucleotides in length and selected so as to be complementary to a sequence of said analyte, and the second, noncomplementary region containing at most about 5 kb in total and including a labelling reagent recognition sequence L-2, wherein each of said sequences L-1 is selected so as to be complementary to physically distinct, nonoverlapping sequences of said analyte; and (b) a labelling reagent having a nucleic acid sequence complementary to said labelling reagent recognition sequence L-2 and a label which provides, directly or indirectly, a detectable signal; and (2) members of a capturing set of reagents comprising:

(a) a plurality of capturing nucleic acid probes comprising single-stranded polynucleotide chains each having two polynucleotide sequence regions, the first region having a nucleic acid sequence C-1 about 15 to about 100 nucleotides in length and which is selected so as to be complementary to a sequence of said analyte, and the second, noncomplementary region containing at most about 5 kb and including a capturing reagent recognition sequence C-2, wherein said sequences L-1 and C-1 are nonidentical, noncomplementary sequences that are each complementary to physically distinct sequences of said analyte;

(b) a capturing reagent having a nucleic acid sequence complementary to said capturing reagent recognition sequence C-2 and containing a first member of a specific binding hapten-antibody pair; and (c) a solid support, to which is bound a second member of said specific binding pair, complementary to said first member, enabling separation and detection of said analyte.

20. The kit of claim 19, wherein said solid support comprises a plurality of particles.

21. The kit of claim 19, wherein said label is a fluorescer or an enzyme.

* * * * *